US006316435B2

(12) United States Patent
Byrd et al.

(10) Patent No.: US 6,316,435 B2
(45) Date of Patent: *Nov. 13, 2001

(54) COMBINATION THERAPY FOR LYMPHOPROLIFERATIVE DISEASES

(75) Inventors: John C. Byrd, Bethesda; Michael R. Grever, Highland; Ian W. Flinn, Lutherville, all of MD (US); Jamie K. Waselenko, San Antonio, TX (US)

(73) Assignee: SuperGen, Inc., Dublin, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/256,666

(22) Filed: Feb. 24, 1999

(51) Int. Cl.[7] ..................... A61K 31/551; A61K 31/553; A61K 31/554; A61K 31/52; A61K 31/195

(52) U.S. Cl. ..................... 514/211.08; 514/264; 514/567

(58) Field of Search ............................... 514/221.08, 264, 514/567

(56) References Cited

PUBLICATIONS

Mentz et al., Blood, 88(6), 2172–2182, Abstract Only, 1996.*
J.C. Byrd et al., "Old and New Therapies in Chronic Lymphocytic Leukemia: Now is the Time for a Reassessment of Therapaeutic Goals", Seminar in Oncology, vol. 25,No. 1;(1998), pp. 65–74.
Byrd, J. et al., "Old and New Therapies in Chronic Lymphocytic Leukemias: Now Is the Time For a Reassessment of Therapeutic Goals", Seminars in Oncology, vol. 25, No. 1, Feb., 1998: pp. 65–74.
Dearden, C. et al., "Deoxycoformycin in the treatment of mature T–cell leukaemias", Br. J. Cancer, 64, 1991, pp. 903–906.
Greiner, D. et al., "Pentostatin (2'–deoxycoformycin) in the treatment of cutaneuos T–cell lymphoma", Journal of the American Academy of Dermatology, vol. 36, No. 6, Part 1, Jun. 1997, pp. 950–955.
Duggan, D.B. et al., "2'Deoxycoformycin (Pentostatin) for Refractory Non–Hodgkin's Lymphoma: A CALGB Phase II Study", Medical and Pediatric Oncology, 18:203–206, 1990, pp. 203–206.
Grever, M. R. et al, "An Investigation of 2'–Deoxycoformycin in the Treatment of Cutaneous T–Cell Lymphoma", Blood, vol. 61, No. 2, Feb. 1983, pp. 279–282.
Grever, M. R. An Investigation of Deoxycoformycin In Advanced Cutaneous T Cell Lymphoma (CTCL), Clinical Research, vol. 33, No. 4, 1985.
Diamandidou, E. et al., "Mycosis Fungoides and Sezary Syndrome", Blood, vol. 88, No. 7, Oct. 1, 1996, pp. 2385–2409.
Kemme, D. J. et al., "State of the Art Therapy of Mycosis Fungoides and Sezary Syndrome", Oncology, vol. 6, Feb. 1992, pp. 31–42.

Byfield, J. E. et al., "Mice, men, mustard and methylated xanthines: the potential role of caffeine and related drugs in the sensitization of human tumours to alkylating agents", Br J Cancer, 43(5), May 1981, pp. 669–683 (Abstract).
Murnane, J. P. et al., "Effects of methylates xanthines on mammalian cells treates with bifunctional alkylating agents", Nature, 285(5763), May 1980, pp. 326–329 (Abstract).
Murnane, J.P. et al., "The structure of methylated xanthines in relation to their effects on DNA synthesis and cell lethality in nitrogen mustard–treated cells", Biophys J, 35(3), Sep. 1981, pp. 665–676 (Abstract).
Musk, S. R. et al., "Override of the radiation–induced mitotic block in human tumour cells by methylxanthines and its relationship to the potentiation of cytotoxicity", Int J Radia Biol, 57(6), Jun. 1990, pp. 1105–1112 (Abstract).
Pardee, A.B., et al., "Interference with DNA repair mechanisms of mammalian cells: cell cycle dependence", Princess Takamatsu Symp, 13, 1983, pp. 287–294 (Abstract).
Murnane, J.P., et al., "Irreparable DNA cross–links and mammalian cell lethality with bifunctional alkylating agents", Chem Biol Interact, 38(1), Dec. 1981, pp. 75–86 (Abstract).
Fox, M., et al., "Drug resistance and DNA repair", Cancer Metastasis Rev, 6(3), 1987, pp. 261–281 (Abstract).
Citti, L., et al., "The relevance of DNA repair in the cytotoxic response of mammalian cells to alkylating agents,",Ann 1st Super Sanita, 25, 1989, pp. 5–9 (Abstract).
Ishiguro, K., et al., "A sensitization effect of hematoporphyrin oligomer (HpO) and caffeine for X–ray radiation of skin cancer", Nippon Hifuka Gakkai Zasshi, 100(6), May 1980, pp. 669–688 (Abstract).
Mentz, F. et al, "Simple, fast method of detection apopotosis in lymphoid cells", Cytometry, 32(2), Jun. 1998, pp. 95–101 (Abstract).
Fujiware, Y., et al, "Replicative bypass repair of ultraviolent damage to DNA of mammalian cells: caffeine sensitive and caffeine resistant mechanisms", Mutat Res, 37(1), Oct. 1976, pp. 91–110, (Abstract).
Ducore, J.M. et al, "Theophylline does not reverse DNA replicon initation inhibtion in human cells resistant to alkylating agent–theophylline killing synergism", Chem Biol Interact, 51(2), Sep. 15, 1984, pp. 191–200 (Abstract).
Gruenerg, D.C. et al., "Repair of ultraviolent damage in human cells also exposed to agents that cause strand breaks, crosslinks, monoadducts and alkylations", Chem Biol Interact, 33(2–3), Jan. 1981, pp. 163–177 (Abstract).
Oesch–Bartlomowicz, B. et al., "Modulation of the control of mutagenic metabolites derived from cyclohosphamide and ifosfamide by stimulation for protein kinase A", Mutat Res, 232(2), Oct. 1990, pp. 305–312 (Abstract).
Clinical Investigations, Proceedings of AACR, vol. 27, Mar. 1986, pp. 780–783.

* cited by examiner

Primary Examiner—Jerome D. Goldberg
(74) Attorney, Agent, or Firm—Wilson Sonsini Goodrich & Rosati; David J. Weitz

(57) ABSTRACT

Disclosed are methods and kits for treating lymphoproliferative diseases in a host including (co)administering to the host pentostatin, at least one alkylating agent and at least one methylated xanthine.

49 Claims, No Drawings

COMBINATION THERAPY FOR LYMPHOPROLIFERATIVE DISEASES

BACKGROUND OF THE INVENTION

1. Field of the Invention

The invention relates to methods and kits for treating lymphoproliferative diseases comprising (co)administering to the host pentostatin, at least one alkylating agent and at least one methylated xanthine.

2. Description of Related Art

In spite of the chemosensitivity seen with the initial treatment of malignant lymphoproliferative diseases, relapse is uniform and death commonly occurs as a result of disease progression. One example of this is Chronic Lymphocytic Leukemia (CLL). CLL is the most common adult leukemia occurring in the western hemisphere and accounts for 25% of all leukemias. The extremely indolent natural history of both smoldering and early stage CLL has left many with the perception that this is a "good leukemia" that can be ignored until the advanced stage at which time palliative therapy is acceptable. K. R. Rai et al., *Clinical Staging of Chronic Lymphocytic Leukemia*, Blood 46:219–234 (1975); J. L. Binet et al., *A New Prognostic Classification of Chronic Lymphocytic Leukemia Derived from a Multivariate Survival Analysis*, Cancer 48:198–216 (1981). This document, and all others cited to herein, are incorporated by reference as if reproduced fully herein.

A contrary interpretation of the available data on CLL is that it is currently an incurable illness with advanced stage patients having a median survival of 18 months to 3 years. J. S. Lee et al., *Prognosis of Chronic Lymphocytic Leukemia: A Multivariate Regression Analysis of 325 Untreated Patients*, Blood 69:929–936 (1987); E. Montserratt et al., *Chronic Lymphocytic Leukemia: Prognostic Factors and Natural History*, Baillieres Clin Haematol 6:849–866 (1993). For the patient younger than 50 years, even the diagnosis of early stage CLL shortens expected survival by an average of 19 years. E. Montserrat et al., *Presenting Features and Prognosis of Chronic Lymphocytic Leukemia in Younger Adults*, Blood 78:1545–1551 (1991).

Disease frequency and expected death rate derived from the Surveillance, Epidemiology, and End Results program further discredit the former paradigm. S. L. Parker et al., *Cancer Statistics, 1997*, CA Cancer J Clin 47:5–27 (1997). Approximately 7,400 patients may have been diagnosed with CLL in the United States during 1997, with 4,300 dying during that same period as a direct result of this disease. This absolute death rate is several times that observed in all combined pediatric tumors and similar or slightly lower than that observed in many adult solid tumors.

The reasons for the incurability of lymphoproliferative diseases may stem from intrinsic biologic drug resistance related to many factors, including inactivation of the p53 tumor suppressor gene and overexpression of the apoptotic protein bcl-2.

Bcl-2 overexpression and aberrant p53 function are frequently observed in low-grade B-cell and T-Cell lymphomas. Tumor overexpression of bcl-2 protein may be associated with marked resistance to apoptosis induced by chemotherapy or radiation and has been associated with a worse outcome. T. Miyashita et al., *Bcl-2 Oncoprotein Blocks Chemotherapy-induced Apoptosis in a Human Leukemia Cell Fine*, Blood 81:151–157 (1993); L. Sachs et Al., *Control of Programmed Cell Death in Normal and Leukemic Cells: New Implications for Therapy*, Blood 82:15–21 (1993); O. Hermine et al., *Prognositic Significance of Bcl-2 Expression in Aggressive Non-hodgkin's Lymphoma*, Blood 87: 265–272 (1996). Aberrant p53 function is also associated with both a poor treatment response and inferior survival in these disorders. K. Dohner et al., p 53 *Gene Deletion Predicts for Poor Survival and Non-response to Therapy with Purine Analogs in Chronic B-cell Leukemias*, Blood 85:1580–1589 (1995); A. Ichikawa et al., *Mutations of the P53 Gene as a Prognostic Factor in Aggressive B-cell Lymphoma*, NEJM 337: 529–34 (1997); E. Wattel et al., p53 *Mutation Are Associated with Resistance to Chemotherapy and Short Survival in Hematologic Malignancies*, Blood 84: 3148–3157 (1994).

In the case of CLL in particular, the central decision of the physician caring for a CLL patient was when to initiate treatment and what schedule of alkylator therapy to use. Results from a large French Cooperative Group study comparing immediate versus delayed chlorambucil therapy in early (Binet A) stage patients showed an inferior survival rate for the patients who had an early therapeutic intervention. French Cooperative Group on Chronic Lymphocytic Leukemia, *Effects of Chlorambucil and Therapeutic Decision in initial Forms of Chronic Lymphocytic Leukemia (Stage A)*, Blood 1414–1421 (1990). This unexpected poor outcome in the patients receiving immediate therapy was partially attributed to a higher frequency of epithelial malignancies.

Once therapeutic intervention has been deemed necessary, the task of deciding what therapy is appropriate for the individual patient is equally challenging. Conventionally, initial treatment of patients with symptomatic CLL has often involved therapy with chlorambucil with or without prednisone. The addition of prednisone is based on a small 26-patient comparative study of chlorambucil versus chlorambucil plus prednisone that noted an improved response rate but similar survival in patients receiving this combination. T. Han et al., *Chlorambucil Versus Combined Chlorambucil-corticosteroid Therapy in Chronic Lymphocytic Leukemia*, Cancer 31:502–508 (1973).

Corticosteroids as a single agent have minimal activity against CLL, predispose the patient to a higher risk of infections, and may aggravate hyperlymphocytosis. P. A. Kyle et al., *Large Doses of Prednisone and Prednisolone in the Treatment of Malignant Proliferative Disorders*, Ann Intern Med 57:717–731 (1962). Comparative trials of combination therapy to single-agent chlorambucil have shown similar or improved response, but no impact on survival. E. Montserrat et al., *Treatment of Chronic Lymphocytic Leukemia in Advanced Stages*, Cancer 56:2369–2375 (1985); The French Cooperative Group on Chronic Lymphocytic Leukemia, A Randomized *Clinical Trial of Chlorambucil Versus COP in Stage B Chronic Lymphocytic Leukemia*, Blood 75:1422 (1990) (abstr); B. Raphael et al., *Comparison of Chlorambucil and Prednisone Versus Cyclophosphamide, Vincristine, and Prednisone as Initial Treatment for Chronic Lymphocytic Leukemia: Long Term Follow-up of the Eastern Cooperative Oncology Group Randomized Clinical Trial*, J Clin Oncol 9:770–776 (1990).

In an attempt to improve CLL treatment, physicians have also turned to the purine analog fludarabine. Results from several large phase II studies led by the MD Anderson Leukemia group and others in previously treated and untreated CLL patients noted a 31% to 57%, and 78% response rate, respectively. M. R. Grever et al., *Fludarabine Monophosphate: A Potentially Useful Agent in Chronic Lymphocytic Leukemia*, Nouv Rev Fr Hematol 30:437–459 (1988); M. J. Keating, *Fludarabine Phosphate in the Treat-* ment of Chronic Lymphocytic Leukemia, Semin Oncol 17:49–62 (1990); M. J. Keating et al., *Fludarabine: A New Agent with Marked Cytoreductive Activity in Untreated Chronic Lymphocytic Leukemia*, J Clin Oncol 9:44–49 (1991).

Attempts to improve on the outcome of therapy in CLL and other hematologic malignancies has occurred through rational combination approaches with utilizing agents with non-overlapping toxicity. Pre-clinical data (Proc Am Ass Cancer Res 38: 2a, 1997, Biochem Pharmacol 44: 2220, 1992) suggest synergistic interaction between DNA damaging agents and the purine analogs or pentostatin. Based on these data, combination studies with alkylating agents and one of the purine analogs have been performed. (Leukemia 8: 1290, 1994; Leukemia 7: 361,1993; Blood 84s: 383a, 1994). With respect to fludarabine, these studies demonstrated that myelosupression was more problematic, and compromised the total administered dose of each agent. Three phase 11 designs were initiated with fludarabine and cyclophosphamide using either greatly attenuated doses of fludarabine and cyclophosphamide (Regimen A, Blood 88s: 480a, 1994), somewhat less attenuated doses of these therapies with filgrastim support (Regimen B, Blood 92s: 104a, 1998) and sequential therapy (cyclophosphamide single agent therapy followed by fludarabine monotherapy (Regimen C, Blood 88s: 481 a, 1996). A summary of response these studies in untreated patients is shown in Table 1 below.

| Reg | Agents Utilized | Number of Patients | % Complete Remission | % Complete + Partial Remission |
|---|---|---|---|---|
| A | FLU + CY | 14 | (30)* | 93 |
| B | FLU + CY + G-CSF | 20 | 50 | 100 |
| C | FLU Then CY | 18 | 33 | 89 |

Key:
Ref—reference; FLU—fludarabine; CY—cyclophosphamide;
*From presentation

Impressive tumor cytoreduction was noted in all series. However, the frequency of complete response rate as compared to that expected with fludarabine monotherapy was not appreciably increased with the attenuated dose or sequential therapy. In a separate study, Oken and colleagues combined the less myelosuppressive agent pentostatin with chlorambucil and prednisone in untreated CLL patients and noted an overall response rate of 87%, including a 44% complete response rate. (Proc Am Soc Clin Oncol 17: 6a, 1998) Unlike many of the combination series reported to date, long term follow-up was available demonstrating a median response duration that had not reached at greater than 32 months. Opportunistic infections were problematic in this study, likely as a consequence of the corticosteroids in the absence of antimicrobial and antiviral prophylaxis.

Accordingly, there still remains room for improvement in the treatment of chronic lymphocytic leukemia, and other lymphoproliferative diseases. Accordingly, there is a need for improvement in treating lymphoproliferative diseases.

DETAILED DESCRIPTION OF THE INVENTION

While precise knowledge of the mechanism of the synergism due to the combination is not necessary to the practice of the invention, a brief discussion of the putative mechanism may be helpful to understanding of the invention. Of course, because precise knowledge of the mechanism is not necessary to the practice of the invention, the inventor expressly does not wish to be bound to any discussion of mechanism present herein.

Generally speaking, the combination of pentostatin, alyklating agents, and methylated xanthines appears to be synergistically more effective in treating lymphoproliferative diseases than monotherapy of any of the three pharmaceuticals alone. Several reasons for this might exist. First of all, the three pharmaceuticals have different putative mechanisms of action, as is discussed further below. This implies that the dosages of each of the three pharmaceuticals may be increased to a point where the total pharmaceutical delivery exceeds the amount that safely can be given of any one of the pharmaceuticals. Additionally, use of the inventive combination therapy may tend to reduce the chances of developing cross-resistance to the various mechanisms of action of the three pharmaceuticals. Such approaches of combination therapies (different than these described herein) in the treatment of other hematologic malignancies has lead to cure in a minority of patients.

At this point, a discussion of the individual components of the inventive combination therapy may be helpful.

While not wishing to be bound by a particular mechanism or explanation, it appears that pentostatin may act through the lymphocyte's adenosine deaminase (ADA) pathways. While ADA is a ubiquitous enzyme, it is found in higher concentrations in lymphoid tissue, particularly T-lymphocytes.

2'-deoxycoformycin (also referred to as DCF, pentostatin, or NIPENT) is a nucleoside analog produced by *Streptomyces antibiotics*, and has been shown to be a quasi-irreversible inhibitor of ADA. By favoring the predominance of deoxycytidine kinase (DCK) over the dephosphorylating enzyme 5-nucleotidase in lymphocytes it is presumed to induce a preferential accumulation of deoxyadenosine-5'-triphosphate (dATP). Dighiero, G., "Adverse and beneficial immunological effects of purine nucleoside analogues," *Hematol Cell Ther*, 38:575–581 (1996).

In humans, a genetic deficiency of adenosine deaminase may cause severe combined immunodeficiency. This enzyme is responsible for deamination of adenosine to inosine and deoxyadenosine to deoxyinosine in the purine salvage pathway. ADA deficiency is characterized by a selective lymphopenia of both T and B cells resulting in reduced cellular and humoral immune capacity, which may be attributed to the toxic effect of deoxyadenosine accumulation.

While the exact nature of the ADA pathway intervention seems unclear, it may be that pentostatin's inhibition of adenosine deaminase might mimic an ADA-deficient state. Lack of ADA is believed to lead to a build up of deoxyadenosine and adenosine triphosphate in the cell, thus fatally accelerating DNA strand breaks in the cell.

Under normal conditions, lymphocytes are continuously breaking and rejoining DNA. When this physiological process is accelerated by the effect of excess adenosine triphosphate, it leads to consumption of NAD for poly-ADP-ribose synthesis. This polymer is produced from nicotinamide adenosine dinucleotides (NAD) in a reaction catalyzed by the chromatin-associated poly(ADP-ribose) synthetase, leading to a depletion of the NAD content of the cell. This depletion induces a profound alteration of cellular reducing power, because of lethal ADP and ATP depletion. The result is programmed cell death through activation of a Ca++, Mg++, dependent endonuclease.

At doses of 5 mg/m$^2$ for 3 consecutive day every 3 weeks, ECOG investigators have been able to show a 32% response rate in refractory lymphomas using pentostatin as a monotherapy. Johnson and colleagues found a 30% response rate in patients with refractory/relapsed B-CLL. Seventeen of 29 of the study patients had prior treatment with either 2-CDA or fludarabine, thus suggesting differential efficacy compared to other purine analogs. Responses seen after treatment with alkylators and other purine analogs demonstrate possible non-cross-resistance. S. Johnson et al., *Phase In Evaluation of 2'deoxycoformycin (Pentostatin) in a Five Day Schedule for the Treatment of Relapsed/Refractory Chronic Lymphocytic Leukemia (Cll)*, Blood:590a (1996).

Most conventional alkylating agents are useful in the practice of this invention. Such alkylating agents include, but are not limited to nitrogen mustards such as chlorambucil, cyclophosphamide, ifosamide, estramustine, mechlorethamine, and melphalan; ethyleneimine derivatives such as triethylenethiophosphoramide (THIOTEPA7, Immunex Corp.); alkyl sulfonates such as busulfan; nitrosureas such as carmustine, lomustine, and streptozocin; triazines such as dacarbazine; metal salts such as platinum compounds (including cisplatin, tertplatin, carboplatin, etc.). In a preferable embodiment, the alkylating agent is a nitrogen mustard. In a more preferable embodiment, the alkylating agent is chlorambucil.

As discussed above, alkylating agents possess a different mechanism of action from pentostatin. Briefly, alkylating agents tend to induce DNA damage via DNA alkylation and the forming of DNA cross links.

In more detail, alkylating agents generally are a diverse group of compounds capable of forming molecular bonds with nucleic acids, proteins, and many molecules of low molecular weight. Alkylating agents are usually either electrophiles or generate electrophiles in vivo to produce polarized molecules with positively charged regions. These polarized molecules can then interact with electron-rich regions of most cellular molecules. The cytotoxic effect of the alkylating agents appears to relate primarily to the interaction between the electrophiles and DNA. This interaction may result in substitution reactions, cross-linking reactions, or strand-breaking reactions. The net effect of the alkylating agent's interaction with DNA is to alter the information coded in the DNA molecule. This alteration results in inhibition or inaccurate replication of DNA with resultant mutation or cell death.

Within the context of the invention, methylated xanthines refers to methylated xanthines, their derivatives and prodrugs thereof. In a preferable embodiment, the methylated xanthines include theophylline, caffeine, theobromine, and paraxanthine. In a more preferable embodiment, the methylated xanthine is theophylline. Methylated xanthines have been reported to enhance the lethal potential of many DNA-damaging agents. J. P. Murnane et al., *Effects of Methylated Xanthines on Mammalian Cells Treated with Bifunctional Alkylating Agents*, Nature 285:326–329 (1980). As a single agent, methylated xanthines have reduced cytotoxic effects (Binet et al). Methylated xanthines may be used in the practice of this invention to enhance the cytotoxic effects of the alkylating agents and the pentostatin.

Based upon the observation of absent CLL progression in a patient receiving the phosphodiesterase inhibitor theophylline, it was subsequently demonstrated (Br J Haematol 90:957, 1995) that theophylline markedly increased spontaneous apoptosis in CLL samples studied in vitro. Further investigation of this observation demonstrated that theophylline given together with chlorambucil (Blood 88: 2172, 1996) yielded in vitro synergistic apoptosis toward human CLL cells. The induction of theophylline-induced apoptosis correlated with an increased intracellular level of cAMP, a known second signal required for programmed cell death and down-regulation of bcl-2 which is a known inhibitor or apoptosis in CLL. (50) A preliminary report (Leukemia 9:2159, 1995) noted no activity utilizing theophylline as a single agent, but its combination with chlorambucil or cyclophosphamide in alkylator-refractory CLL yielded responses in 11 of 12 patients.

The mechanism by which methylated xanthines function remains unclear. Some investigators believe that they exert their potentiating effect either by directly inhibiting repair of damage in DNA or by causing override of the radiation-induced inhibition of DNA synthesis. S. R. et al., *Override of the Radiation-induced Mitotic Block in Human Tumour Cells by Methylxanthines and its Relationship to the Potentiation of Cytotoxicity*, Int. J. Radiat. Biol. 57:1105–1112 (1990). There is also evidence that methyl xanthine compounds can potentiate cytoxocity of chemotherapy in p53 deficient cells through abrogation of the G2 cell cycle checkpoint. Additionally, methylated xanthine administration may result in accumulation of intracellular cAMP that activates the apoptosis cascade. F. Mentz et al., *Theophylline Synergies with Chlorambucil in Inducing Apoptosis of Bchronic Lymphocytic Leukemia Ceffs*, Blood 88:2172–2182 (1996). Of course, precise understanding of the mechanism of action is not necessary to the practice of this invention.

Pentostatin may be obtained from commercial suppliers, including SuperGen, Inc. (San Ramon, Calif.) which supplies pentostatin under the trademark NIPENT. Alkylating agents and methylated xanthines according to the invention are available from commercial suppliers, based upon information present in, for example, the Physician's Desk Reference. A more preferable alkylating agent, chlorambucil, is available as LEUKERAN from Burroughs Wellcome. A preferable methylated xanthine, theophylline, is available in tablets from Rhone-Poulenc Rorer.

The alkylating agents according to the invention may be preferably administered in an amount effective to treat a lymphoproliferative condition in a host, alone or in combination. In a more preferable embodiment, the alkylating agents according to the invention may be administered in an amount ranging from about 1 mg/m$^2$ to about the maximum tolerated dosage for the alkylating agent. In a still more preferred embodiment, the alkylating agents according to the invention may be administered in an amount ranging from about 10 mg/m$^2$ to about 1000 mg/m$^2$. In a yet more preferred embodiment, the alkylating agents according to the invention may be administered in an amount ranging from about 20 mg/m$^2$ to about 40 mg/m$^2$.

The methylated xanthines according to the invention may be preferably administered in an amount effective to treat a lymphoproliferative condition in a host, alone or in combination. In a more preferable embodiment, the methylated xanthines according to the invention may be administered in an amount ranging from about 1 mg/kg to about the maximum tolerated dosage for the methylated xanthine. In a still more preferred embodiment, the methylated xanthines according to the invention may be administered in an amount ranging from about 1 mg/kg to about 10 mg/kg. In a yet more preferred embodiment, the methylated xanthines according to the invention may be administered in an amount ranging from about 2 mg/kg to about 5 mg/kg. In an especially preferred embodiment, the methylated xanthines according to the invention are administered in a first dose at 5 mg/kg, followed by subsequent doses of 2–3 mg/kg every 6–8 hours. The serum level of theopylline will be approximately 10–20 ug/ml during treatment.

Pentostatin, according to the invention, may be preferably administered in an amount effective to treat a lymphoproliferative condition in a host, alone or in combination. In a more preferable embodiment, pentostatin according to the invention may be administered in an amount ranging from about 0.1 mg/m$^2$ to about the maximum tolerated dosage for pentostatin. In a still more preferred embodiment, pentostatin according to the invention may be administered in an amount ranging from about 1 mg/m$^2$ to about 4 mg/m$^2$. In a yet more preferred embodiment, pentostatin according to the invention may be administered in an amount ranging from about 2 mg/m$^2$ to about 3 mg/m$^2$.

The alkylating agents, methylated xanthines and pentostatin according to the invention may be administered by a variety of routes, and may be administered or coadministered in any conventional dosage form. Coadministration in the context of this invention is defined to mean the administration of more than one therapeutic in the course of a coordinated treatment to achieve an improved clinical outcome. Such coadministration may also be coextensive, that is, occurring during overlapping periods of time. (Co) administration may be taken to mean either coadministration or administration or both.

For example, the alkylating agents, methylated xanthines and pentostatin according to the invention may be administered via a coordinated cycle of medication. In a preferable embodiment, the methylated xanthines are administered for nine days, and the alkylating agents and pentostatin are administered on the eighth day of the nine day methylated xanthine regimen. In another preferable embodiment, this nine day cycle is repeated once every twenty-one days. In a still more preferable embodiment, the nine day cycle is repeated once every twenty-one days for a maximum of six cycles.

The alkylating agents, methylated xanthines and pentostatin according to the invention may be administered or coadministered in any conventional dosage form. For example, they may be administered or coadministered parenterally, orally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, or intrathecally. The alkylating agents, methylated xanthines and pentostatin according to the invention may also be administered or coadministered in slow release dosage forms. Furthermore, alkylating agents, methylated xanthines and pentostatin may be administered or coadministered with conventional pharmaceutical excipients and additives. As alkyating agents and pentostatin may induce nausea and vomiting, addition of a serotonin blocking agent (Kytril or Odansetron) may be considered on the 8$^{th}$ day. Additionally, as infection may develop while receiving this therapy in previously treated patients, consideration of treating with prophylactic antibiotics should be given.

A wide variety of lymphoproliferative diseases may be treated in the practice of this invention, although greatest efficacy has been observed thus far in B-cell chronic lymphocytic leukemia (3 of 4 responses for 75% response rate). Such diseases include, but are not limited to, low-grade lymphoproliferative disorders, chronic lymphocytic leukemias, cutaneous T cell leukemias including Sezary, hairy cell leukemias, lymphomas, Non-Hodgkin's lymphomas, and large granular lymphocytic leukemias, hairy cell leukemia, splenic lymphoma with vilous lymphocytes, Waldenstrom's macroglobulinemia and p53 deficient hematologic malignancy tumors.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents. Additionally, the following examples are appended for the purpose of illustrating the claimed invention, and should not be construed so as to limit the scope of the claimed invention.

EXAMPLES

Example 1

Treatment according to the invention has occurred through an ongoing phase I clinical trial performed at Walter Reed Army Medical Center and The Johns Hopkins Oncology Center. In this study, patients with low-grade lymphoproliferative disorders have been treated using the combination of theophylline (dosed to a serum level of 10–20 ug/ml) on days 1–9, pentostatin 2–4 mg/m2 day 8 and chlorambucil 20 mg/m2 day 8. Assessment of in vivo modulation of bcl-2 (whose over-expression correlates with drug resistance and poor outcome in CLL) and p27 occurred at the pretreatment, day 3, day 8, day 9 and day 15 of treatment.

Thus far, 14 patients have been enrolled on the clinical study for whom data are available on 10 related to toxicity and efficacy of treatment. Specifically, this study has identified the dose limiting toxicity of this combination approach to be myelosuppression. Decreased expression of bcl-2 and p27 protein has been noted in vivo in patients responding to therapy thus demonstrating a correlation with in vitro and in vivo efficacy and a potential similar mechanism of action. Responses have been noted in 3 of 4 CLL patients of whom 1 had fludarabine-refractory disease for which no effective therapy exists. This combination therapy appears to be quite active clinically, has a favorable toxicity profile, and is easily administered to patients in the outpatient setting as compared to other therapies utilized for the late treatment of CLL.

Example 2

An 80-year old man presents with B cell chronic lymphocytic leukemia. The patient is administered five mg/kg caffeine for a nine day cycle. On day eight, 2 mg/m$^2$ pentostatin is administered intravenously, together with 25 mg/m$^2$ chlorambucil, also administered intravenously. The nine-day regimen is repeated once every twenty-one days for a total of six cycles or until the patient's disease is stabilized or is in remission.

Example 3

A 26-year old woman presents with adult T-cell leukemia/lymphoma. The patient is administered seven mg/kg theophylline for a nine day cycle. On day eight, four mg/m$^2$ pentostatin is administered intravenously, together with 35 mg/m$^2$ chlorambucil, administered PO. The nine-day regimen is repeated once every twenty-one days for a total of six cycles or until the patient's disease is stabilized or is in remission.

Example 4

An 72-year old man presents with B cell Waldenstrom's macroglobulinemia. The patient is administered five mg/kg theophylline for a nine day cycle. On day eight, 2 mg/m² pentostatin is administered intravenously, together with 20 mg/m² chlorambucil administered PO. The nine-day regimen is repeated once every twenty-one days for a total of six cycles or until the patient's disease is stabilized or is in remission.

Example 5

An 70 year old man presents with NHL. The patient is administered five mg/kg theophylline for a nine day cycle. On day eight, 2 mg/m² pentostatin is administered intravenously, together with 25 mg/m² chlorambucil, administered orally. The nine-day regimen is repeated once every twenty-one days for a total of six cycles or until the patient's disease is stabilized or is in remission.

What is claimed is:

1. A method of treating lymphoproliferative diseases in a host comprising (co)administering to the host a pharmaceutically effective and synergistic amount of pentostatin, chlorambucil and a methylated xanthine.

2. The method of claim 1, wherein chlorambucil is (co)administered in an amount ranging from about 1 mg/m² to about a maximum tolerated dosage for chlorambucil.

3. The method of claim 1, wherein chlorambucil is (co)administered in an amount ranging from about 10 mg/m² to about 1000 mg/m².

4. The method of claim 1, wherein chlorambucil is (co)administered in an amount ranging from about 20 mg/m² to about 40 mg/m².

5. The method of claim 1, wherein the methylated xanthine is selected from the group consisting of theophylline, caffeine, theobromine, and paraxanthine.

6. The method of claim 5, wherein the methylated xanthine is theophylline.

7. The method of claim 1, wherein the methylated xanthine is (co)administered in an amount ranging from about 1 mg/kg to about a maximum tolerated dosage for the methylated xanthine.

8. The method of claim 1, wherein the methylated xanthine is (co)administered in an amount ranging from about 1 mg/kg to about 10 mg/kg.

9. The method of claim 8, wherein the methylated xanthine is (co)administered in an amount ranging from about 2 mg/kg to about 5 mg/kg.

10. The method of claim 9, wherein the methylated xanthine is (co)administered in a first dose of about 5 mg/kg, followed by subsequent doses of about 2 to about 3 mg/kg every about 6 to about 8 hours.

11. The method of claim 1, wherein pentostatin is (co) administered in an amount ranging from about 0.1 mg/m² to about a maximum tolerated dosage for pentostatin.

12. The method of claim 1, wherein pentostatin is (co) administered in an amount ranging from about 1 mg/m² to about 4 mg/m².

13. The method of claim 12, wherein pentostatin is (co)administered in an amount ranging from about 2 mg/m² to about 3 mg/m².

14. The method of claim 1, wherein pentostatin is (co) administered parenterally, orally, intraperitoneally, intravenously, intraarterially, transdermally, intramuscularly, liposomally, via local delivery by catheter or stent, subcutaneously, intraadiposally, or intrathecally.

15. The method of claim 14, wherein pentostatin is (co)administered intravenously.

16. The method of claim 15, wherein the methylated xanthine is (co)administered orally.

17. The method of claim 1, wherein the methylated xanthine is (co)administered parenterally, orally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, or intrathecally.

18. The method of claim 1, wherein chlorambucil is (co)administered parenterally, orally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, or intrathecally.

19. The method of claim 18, wherein chlorambucil is (co)administered intravenously.

20. The method of claim 1, wherein the lymphoproliferative disease is selected from the group consisting of low-grade lymphoproliferative disorders, chronic lymphocytic leukemias, cutaneous T cell leukemias, Sezary syndrome, hairy cell leukemias, lymphomas, Non-Hodgkin's lymphomas, and large granular lymphocytic leukemias.

21. The method of claim 20, wherein the lymphoproliferative disease comprises chronic lymphoproliferative diseases.

22. The method of claim 21, wherein the lymphoproliferative disease comprises cutaneous T cell leukemias.

23. A kit comprising pentostatin, chlorambucil and a methylated xanthine in a pharmaceutically effective and synergistic amount.

24. The kit of claim 23, wherein the methylated xanthine is theophylline.

25. A method of treating lymphoproliferative diseases in a host comprising (co)administering to the host a pharmaceutically effective and synergistic amount of pentostatin, theophyline, and an alkylating agent.

26. The method of claim 25, wherein the alkylating agent is selected from the group consisting of nitrogen mustards, ethyleneimine derivatives, alkyl sulfonates, nitrosureas; triazines, and metal salts.

27. The method of claim 26, wherein the nitrogen mustards comprise chlorambucil, cyclophosphamide, ifosamide, estramustine, mechlorethamine, or melphalan.

28. The method of claim 25, wherein the alkylating agent is (co)administered in an amount ranging from about 1 mg/m² to about a maximum tolerated dosage for the alkylating agent.

29. The method of claim 25, wherein the alkylating agent is (co)administered in an amount ranging from about 10 mg/m² to about 1000 mg/m².

30. The method of claim 25, wherein the alkylating agent is (co)administered in an amount ranging from about 20 mg/m² to about 40 mg/m².

31. The method of claim 25, wherein theophyline is (co)administered in an amount ranging from about 1 mg/kg to about a maximum tolerated dosage for theophyline.

32. The method of claim 25, wherein theophyline is (co)administered in an amount ranging from about 1 mg/kg to about 10 mg/kg.

33. The method of claim 25, wherein theophyline is (co)administered in an amount ranging from about 2 mg/kg to about 5 mg/kg.

34. The method of claim 25, wherein theophyline is (co)administered in a first dose of about 5 mg/kg, followed by subsequent doses of about 2 to about 3 mg/kg every about 6 to about 8 hours.

35. The method of claim 25, wherein pentostatin is (co)administered in an amount ranging from about 0.1 mg/m² to about a maximum tolerated dosage for pentostatin.

36. The method of claim 25, wherein pentostatin is (co)administered in an amount ranging from about 1 mg/m$^2$ to about 4 mg/m$^2$.

37. The method of claim 25, wherein pentostatin is (co)administered in an amount ranging from about 2 mg/m$^2$ to about 3 mg/m$^2$.

38. The method of claim 25, wherein pentostatin is (co)administered parenterally, orally, intraperitoneally, intravenously, intraarterially, transdermally, intramuscularly, liposomally, via local delivery by catheter or stent, subcutaneously, intraadiposally, or intrathecally.

39. The method of claim 25, wherein pentostatin is (co)administered intravenously.

40. The method of claim 25, wherein theophyline is (co)administered parenterally, orally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, or intrathecally.

41. The method of claim 25, wherein theophyline is (co)administered orally.

42. The method of claim 25, wherein the alkylating agent is (co)administered parenterally, orally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, or intrathecally.

43. The method of claim 25, wherein the alkylating agent is (co)administered intravenously.

44. The method of claim 25, wherein the lymphoproliferative disease is selected from the group consisting of low-grade lymphoproliferative disorders, chronic lymphocytic leukemias, cutaneous T cell leukemias, Sezary syndrome, hairy cell leukemias, lymphomas, Non-Hodgkin's lymphomas, and large granular lymphocytic leukemias.

45. The method of claim 25, wherein the lymphoproliferative disease comprises chronic lymphoproliferative diseases.

46. The method of claim 25, wherein the lymphoproliferative disease comprises cutaneous T cell leukemias.

47. A kit comprising pentostatin, theophyline and an alkylating agent in a pharmaceutically effective and synergistic amount.

48. The kit of claim 47, wherein the alkylating agent is selected from the group consisting of nitrogen mustards, ethyleneimine derivatives, alkyl sulfonates, nitrosureas; triazines, and metal salts.

49. The kit of claim 48, wherein the nitrogen mustards comprise chlorambucil, cyclophosphamide, ifosamide, estramustine, mechlorethamine, or melphalan.

* * * * *